(12) United States Patent
Adamchuk et al.

(10) Patent No.: US 10,495,568 B2
(45) Date of Patent: Dec. 3, 2019

(54) APPARATUS FOR ANALYZING A SAMPLE OF GRANULAR MATERIAL

(71) Applicant: THE ROYAL INSTITUTION FOR THE ADVANCEMENT OF LEARNING/MCGILL UNIVERSITY, Montréal (CA)

(72) Inventors: Viacheslav Adamchuk, Ste-Anne-de-Bellevue (CA); Asim Biswas, Guelph (CA); Long Qi, Ste-Anne-de-Bellevue (CA); Maxime Leclerc, Mirabel (CA); Bharath Sudarsan, Fredericton (CA); Wenjun Ji, Ste-Anne-de-Bellevue (CA)

(73) Assignee: THE ROYAL INSTITUTION FOR THE ADVANCEMENT OF LEARNING/MCGILL UNIVERSITY, Montreal (CA)

( * ) Notice: Subject to any disclaimer, the term of this patent is extended or adjusted under 35 U.S.C. 154(b) by 0 days.

(21) Appl. No.: 15/964,972

(22) Filed: Apr. 27, 2018

(65) Prior Publication Data
US 2018/0313747 A1 Nov. 1, 2018

Related U.S. Application Data

(60) Provisional application No. 62/491,461, filed on Apr. 28, 2017.

(51) Int. Cl.
*G01N 21/27* (2006.01)
*G01N 21/25* (2006.01)
(Continued)

(52) U.S. Cl.
CPC ............. *G01N 21/27* (2013.01); *G01N 15/00* (2013.01); *G01N 15/0227* (2013.01);
(Continued)

(58) Field of Classification Search
CPC .... G01N 21/27; G01N 15/00; G01N 15/0227; G01N 15/1468; G01N 21/253;
(Continued)

(56) References Cited

U.S. PATENT DOCUMENTS

2015/0355084 A1  12/2015  Richard
2016/0153954 A1   6/2016  Leslie et al.
(Continued)

FOREIGN PATENT DOCUMENTS

CN  103630441   3/2014
CN  102967694  10/2014
(Continued)

OTHER PUBLICATIONS

Indian application No. IN259/DEL/2015, filed Jan. 29, 2015.

*Primary Examiner* — Jamil Ahmed
(74) *Attorney, Agent, or Firm* — Norton Rose Fulbright Canada (57) ABSTRACT

An apparatus for analysing a sample of granular material, such as soil, is described. An elongated housing has a channel extending therethrough to define an optical path. A cavity is defined within the top of the housing to receive the sample, and a transparent sample-receiving surface is disposed within the cavity at a first elevation from the bottom of the housing. A lens assembly is positioned within the optical path at a second, lower, elevation. The lens assembly magnifies an image formed by light beams reflected by or transmitted through the sample. An image capturing device is disposed across the optical path at a third elevation that is lower than the second elevation. The image capturing device is thus lower than both the lens assembly and the transparent sample-receiving surface. A light source is mounted within the housing to emit light toward the sample-receiving surface.

13 Claims, 5 Drawing Sheets

(51) Int. Cl.
*G01N 33/24* (2006.01)
*G06T 7/90* (2017.01)
*G01N 15/00* (2006.01)
*G01N 21/47* (2006.01)
*G01N 15/14* (2006.01)
*G01N 15/02* (2006.01)

(52) U.S. Cl.
CPC ....... *G01N 15/1468* (2013.01); *G01N 21/253* (2013.01); *G01N 21/4738* (2013.01); *G01N 33/24* (2013.01); *G06T 7/90* (2017.01); *G01N 21/251* (2013.01); *G01N 2015/03* (2013.01); *G01N 2015/1472* (2013.01); *G01N 2021/4769* (2013.01)

(58) Field of Classification Search
CPC .. G01N 21/4738; G01N 33/24; G01N 21/251; G01N 2015/03; G01N 2015/1472; G01N 2021/4769; G06T 7/90
See application file for complete search history.

(56) References Cited

U.S. PATENT DOCUMENTS

2016/0231171 A1* 8/2016 Assefa .................. G01J 3/0272
2016/0248951 A1  8/2016 Fletcher et al.

FOREIGN PATENT DOCUMENTS

| | | |
|---|---|---|
| CN | 103048241 | 10/2014 |
| CN | 203894070 | 10/2014 |
| CN | 104215600 | 12/2014 |
| CN | 103226088 | 4/2015 |
| CN | 204270560 | 4/2015 |
| CN | 204594856 | 8/2015 |
| CN | 105093514 | 11/2015 |
| CN | 204758912 | 11/2015 |
| CN | 105136796 | 12/2015 |
| CN | 105181538 | 12/2015 |
| CN | 205027634 | 2/2016 |
| CN | 205049413 | 2/2016 |
| CN | 205049811 | 2/2016 |
| CN | 102566029 | 3/2016 |
| CN | 104048980 | 4/2016 |
| CN | 105548031 | 5/2016 |
| CN | 105898124 | 8/2016 |
| CN | 105899992 | 8/2016 |
| CN | 205507206 | 8/2016 |
| CN | 104331922 | 3/2017 |
| JP | 2016505890 | 2/2016 |
| JP | 201670714 | 5/2016 |
| KR | 20160069379 | 6/2016 |
| WO | 2016032431 | 3/2016 |
| WO | 2016061563 | 4/2016 |

* cited by examiner

APPARATUS FOR ANALYZING A SAMPLE OF GRANULAR MATERIAL

CROSS-REFERENCE TO RELATED APPLICATIONS

The present application claims priority on U.S. Patent Application No. 62/491,461 filed Apr. 28, 2017, the entire contents of which are incorporated herein by reference.

TECHNICAL FIELD

The application relates generally to soil analyzers and, more particularly, to an optical soil analyzer.

BACKGROUND OF THE ART

Soil texture analysis, which may measure particle size distribution, can be an expensive analytical procedure. Three primary methods accepted by certified soil analysis labs are hydrometer-based sedimentation, pipette method, and laser-based optical techniques. The first two methods require substantial labour, while the third is mostly conducted using costly equipment.

SUMMARY

In one aspect, there is provided an apparatus for analysing a sample of granular material, the apparatus comprising: an elongated housing extending between a top and an bottom spaced apart axially along a longitudinal axis, and a channel extending through the elongated housing to define an optical path; a cavity defined within the top of the housing to receive the sample, the cavity being at least partially open to a surrounding of the apparatus; a transparent sample-receiving surface disposed within the cavity at a first elevation from the bottom along the longitudinal axis, the transparent sample-receiving surface being in optical communication with the optical path; a lens assembly positioned within the optical path and extending thereacross at a second elevation from the bottom along the longitudinal axis, the lens assembly magnifying an image formed at least by light beams reflected by or transmitted through the sample, the second elevation being smaller than the first elevation such that the lens assembly is lower than the transparent sample-receiving surface; an image capturing device disposed across the optical path at a third elevation from the bottom along the longitudinal axis to capture an image, the third elevation being smaller than the second elevation such that the image capturing device is lower than both the lens assembly and the transparent sample-receiving surface; and a light source mounted within the housing to emit light toward the sample-receiving surface.

BRIEF DESCRIPTION OF THE DRAWINGS

Reference is now made to the accompanying figures in which.

DETAILED DESCRIPTION

An apparatus for analyzing a soil sample is described. The apparatus 10 is configured to analyze an image of the soil sample 12 and quantifiably measure, and not simply estimate, the composition of the soil sample. This is done by measuring the texture of the soil sample to determine the number of soil particles present and their size, thereby permitting the present apparatus to calculate a percentage of each category (e.g. sand, clay, silt, etc.) of soil particles within the soil sample.

The soil sample 12 can be collected from a field and transported to a laboratory for analysis. Optionally, the apparatus 10 can be transported to the field for in-situ soil analysis. The soil sample 12 can contain a number of different soil particles, such as, but not limited to, sand, silt and clay. Other particles can however also be present in the soil sample 12, such as gravel and organic matter such as plant residue. Nevertheless, each soil particle can be categorised into a predetermined category based on its size (e.g. the diameter of the particle), such as a "sand category" containing sand particles, a "silt category" containing silt particles, and a "clay category" containing clay particles. Each of the particle type categories will have particles of a given size range. In a particular embodiment, for example, the sand particles will be identified as those particles having a size above 50 micrometers, the clay particles will be identified as those particles having a size less than 2 micrometers, and the silt particles will be identified as those particles having a size between those of the sand and clay particles (i.e. between 50 micrometers and 2 micrometers). In a particular embodiment, the soil sample 12 may weigh, for example five grams.

Figure 1:
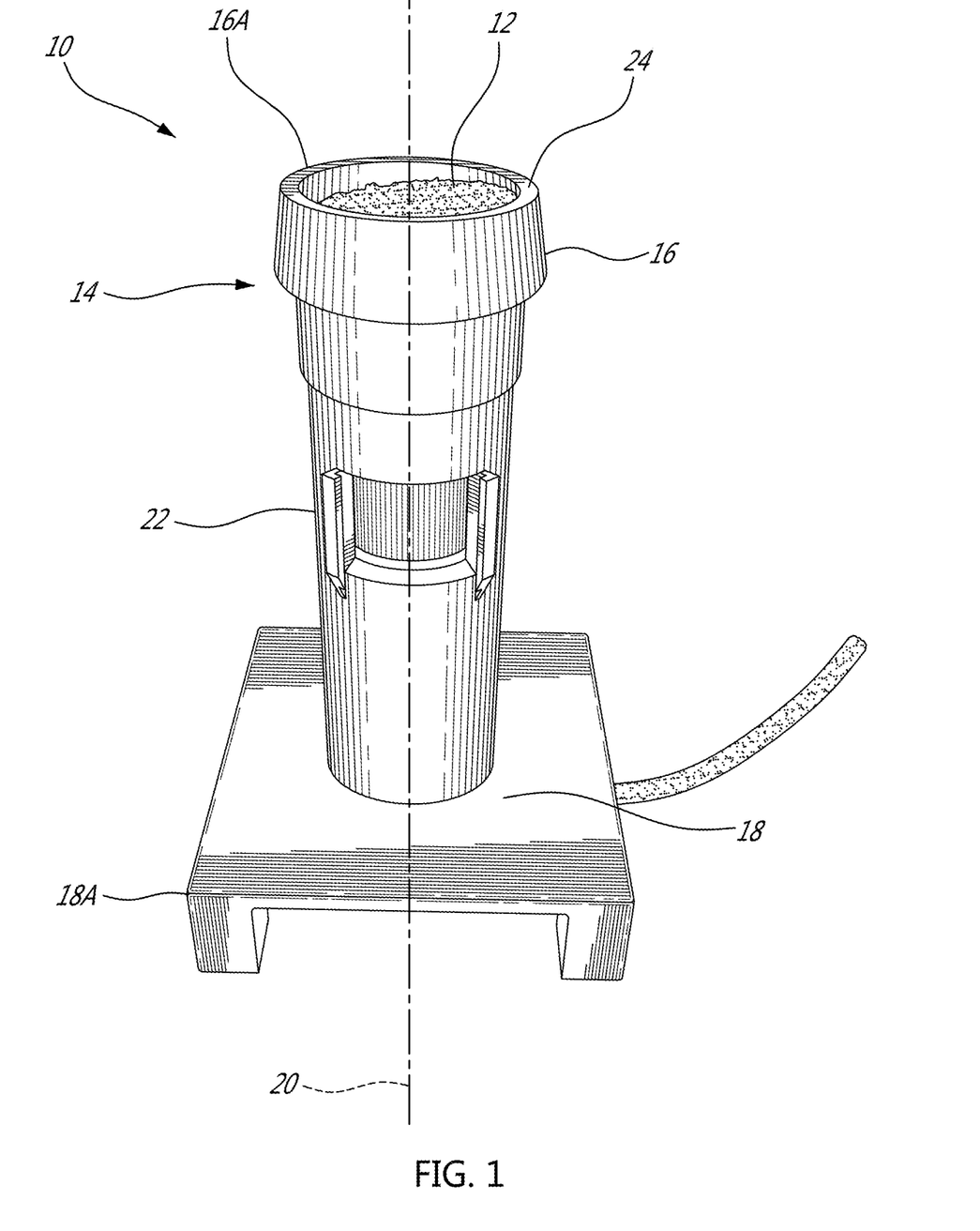
FIG. 1 is a perspective view of an apparatus for analyzing a soil sample, in accordance to a particular embodiment.
Figure 4:
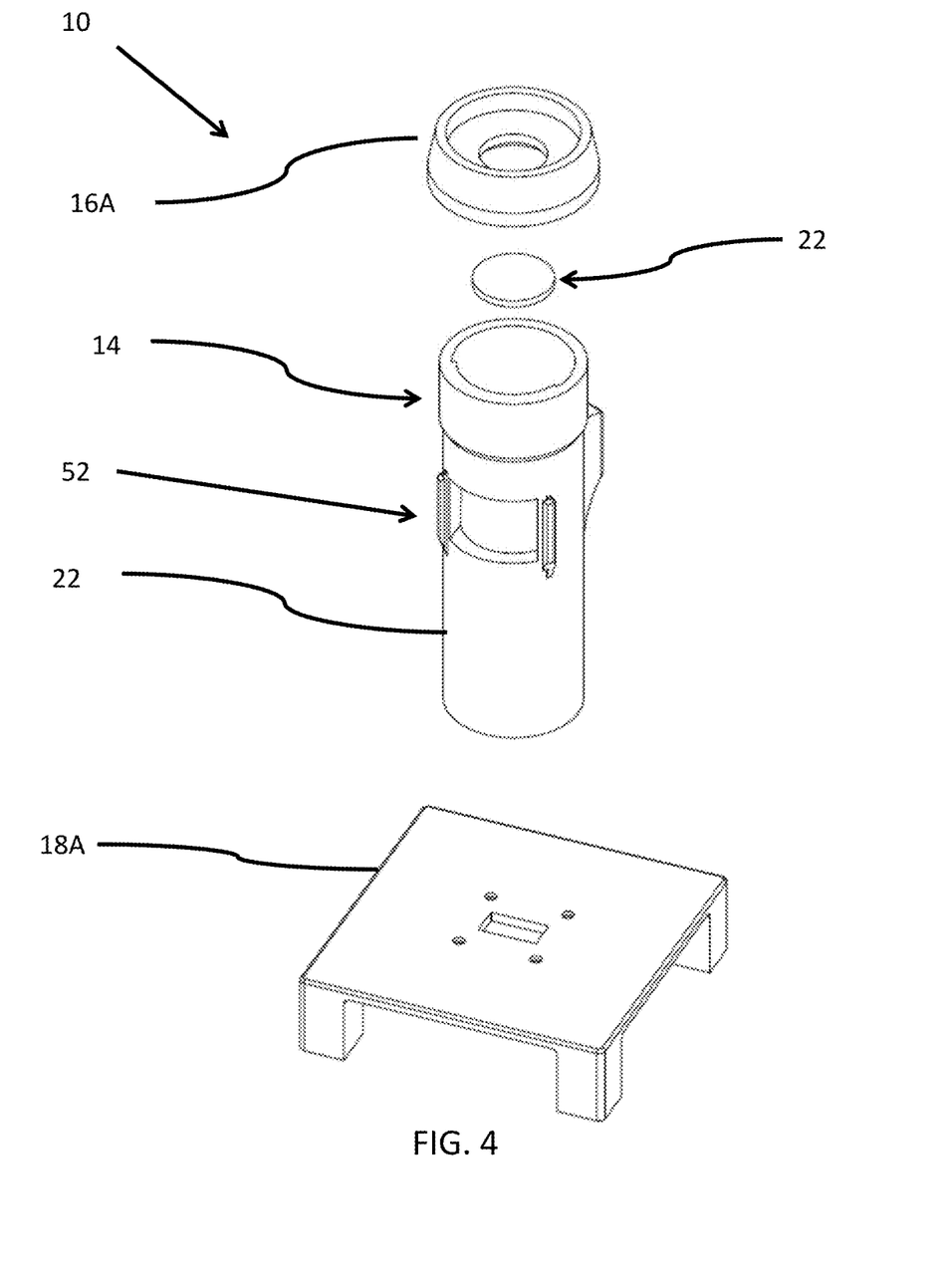
FIG. 4 is a partially exploded perspective view of the apparatus of FIG. 1.

Referring to FIGS. 1 and 4, the apparatus 10 for analyzing a soil sample 12 includes generally an elongated housing 14 extending vertically between two opposite ends, namely an upper end 16 and a lower end 18, along a longitudinal axis 20. The housing 14 includes a head 16A at the upper end 16, a base 18A at the opposed lower end 18 and an elongated body 22 between the head 16A and the base 18A. The head 16A has an outermost surface 24 delimiting an outermost, and uppermost, surface of the apparatus 10.

Figure 2A:
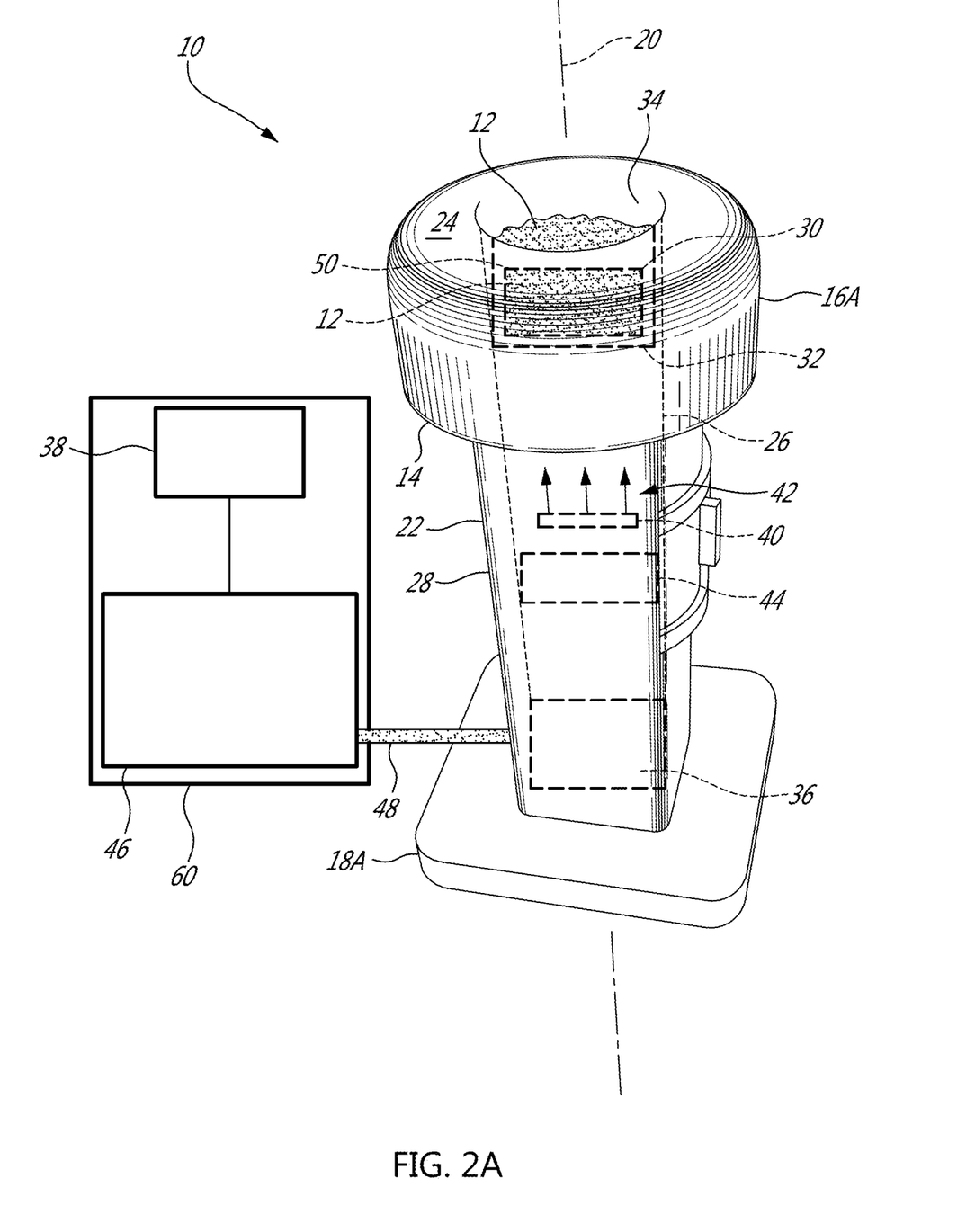
FIG. 2A is a schematic and partially sectioned perspective view of the apparatus shown in FIG. 1.
Figure 2B:
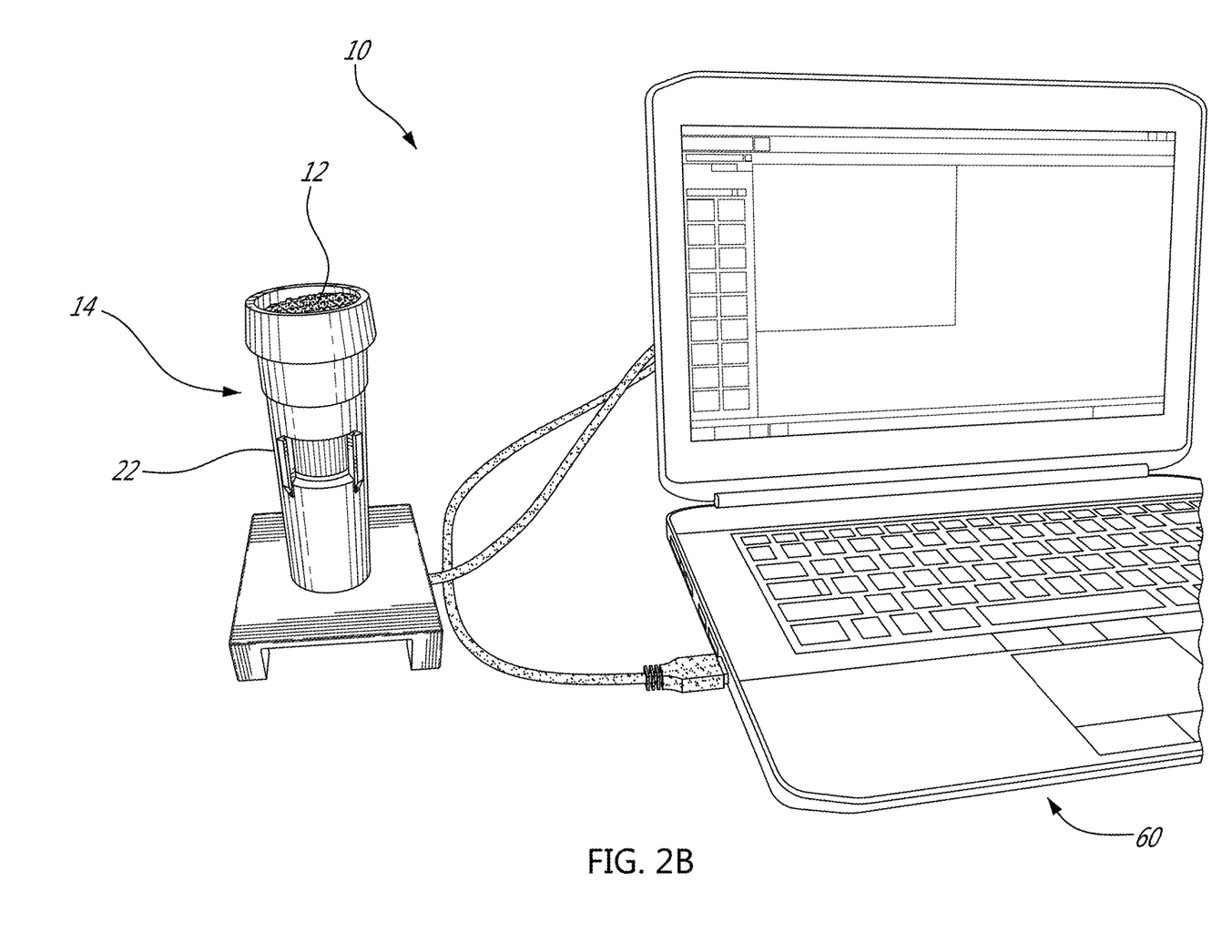
FIG. 2B is another perspective view of the apparatus of FIG. 2A.

Referring now to FIGS. 2A and 2B, the housing 14 has an optical path 26 defined through the housing 14 along the longitudinal axis 20. In the embodiment shown, the optical path 26 is a straight channel enclosed by a side wall 28 of the housing 14, the base 18A and the head 16A. A cavity 30 is defined within the housing 14 toward the head 16A for receiving the soil sample 12. The housing 14 has a transparent window 32, which provides a transparent sample-receiving surface, positioned transversely across the optical path 26. In one embodiment, the transparent sample receiving surface 32 extends substantially perpendicularly to the longitudinal axis 20. The sample-receiving surface of the transparent window 32 defines a seat or a bottom of the cavity 30 when the apparatus 10 is positioned upright, as shown in FIGS. 1 and 2. The window 32 is positioned in optical communication with the cavity 30 and in optical communication with the optical path 26. Optical communication through the window 32 implies that light can propagate from one side of the window 32 to the other, e.g. from the cavity 30 to the optical path 26. In use, the soil sample 12 is placed in the cavity 30 on top of, and in contact with, the window 32. The window 32 is made from a scratch resistant material, such as hardened glass. In another particular embodiment, a scratch resistant material is applied to the surface(s) of the window 32.

In the embodiment shown, the housing 14 has an opening 34 defined between the uppermost surface 24 and the cavity 30. The opening 34 forms an "access channel" to the cavity 30 from an exterior of the apparatus 10. Thus, the soil sample 12 is introduced into the cavity 30 through the opening 34. In alternate embodiments, the opening 34 is disposed on a side wall of the head 16A. When moisture is present in the soil sample 12, the moisture can escape from the soil sample 12 through the opening 34. This accordingly prevents moister build-up in the soil sample 12. Gravel and plant residue particles can also be removed from the soil sample 12 directly from the opening 34. In the embodiment shown, the opening 34 and the transparent window 32 are substantially aligned with each other, for example they may both be co-axial and centered with the longitudinal axis 20. In an alternate embodiment, the opening 34 may however be omitted from the apparatus 10 and the head 16A of the housing 14 may be detachable from the body 22 to introduce the soil sample 12 into the cavity 30. When the opening 34 is omitted, however, small apertures are defined within the head 16A of the housing 14 to allow moisture to escape from the soil sample 12. In all cases, therefore, the soil sample in place on the transparent window 32 must be at least partially open to atmosphere, and more particularly such that there is substantially nothing superimposed vertically overtop of the sample which might prevent moisture from escaping from the soil sample.

The apparatus 10 includes an image capturing device 36 positioned across the optical path 26 toward the base 18A. The image capturing device 36 is a device capable of capturing an image or sequence of images, e.g. a still or video image. The image capturing device 36 may include a digital camera. The image capturing device 36 is operable to capture the image in color, grey-scale and/or black and white. The image of the soil sample 12 in the cavity 30 observed through the window 32 is formed by light beams reflected by or transmitted through the soil sample 12. The light beams travel to the image capturing device 36 within the optical path 26 and through the window 32. The image resolution captured by the image capturing device 36 is known or can be determined. In a particular embodiment, the image resolution is around two micrometers. The image provides texture information of the soil particles. The texture information includes, inter alia, the size of each soil particle captured by the image. Each category has a predetermined texture identification such as the particle size. The image capturing device 36 is disposed in communication, such as wireless communication for example, with a storage device 38 configured for storing the image(s). This storage device may include, for example, a cloud database 38. Other storing mechanism can be used. In a particular embodiment, the image capturing device 36 provides the image with resolutions up to 2560×1920 without compression.

The apparatus 10 includes a light source 40 capable of emitting light toward the window 32. The light source 40 can be any device capable of emitting pulsed and/or continuous light. In the embodiment shown, the light source 40 includes an array of light emitting diodes 42. In alternate embodiments, the light source 40 can include one or more of a conventional incandescent light bulb, a fluorescent lamp, a xenon arc lamp, and the like. In the embodiment shown, the light source 40 is mounted in the housing 14 between the cavity 30 and the image capturing device 36. In a particular embodiment, the light source 40 is near the base 18A, to provide light beams toward the window 32 and consequently toward the soil particles in the cavity 30. At least a portion of the emitted light beams are reflected by the soil sample 12 toward the image capturing device 36. The portion of the reflected light beams emitted by the light source 40 is captured in the image of the soil sample 12. In a particular embodiment, the light source 40 is a flexible LED providing illumination by offering independent on/off control to each one of the array of light emitting diodes 42. The light source 40 provides different levels of intensity adjustment capability.

The apparatus 10 includes a lens assembly 44 positioned across the optical path 26, between the cavity 30 and the image capturing device 36. In a particular embodiment, the lens assembly 44 is equidistant from the window 32 and the image capturing device 36. The lens assembly 44 includes one or more of refractive optical bodies for magnifying the image through focusing and/or dispersing the light beams. The level of magnification is generally known based on the configuration of the lens assembly 44. In a particular embodiment, the lens assembly 44 provides a range of 20-220× magnifications.

The apparatus 10 includes an image processing unit 46 in communication with the image capturing device 36. The image processing unit 46 is configured for receiving the image from the image capturing device 36 and measuring the percentage of the soil particles according to predefined size intervals based on the texture information of the soil particles captured by the image. In the embodiment shown, the image processing unit 46 is an external unit 60 from the housing 14 and is connected to the image capturing device by a suitable data-transmission cable 48. This external unity 60 may include, for example, a computer as shown in FIG. 2B. In an alternate embodiment, the connection between the image capturing device 36 and the image processing unit 46 is wireless. In a further alternate embodiment, the image processing unit 46 is integrated directly into, and thus mounted within, the housing 14.

The image processing unit 46 includes a processor on which is run a software comprising an algorithm that uses an adapted wavelet decomposition technique to measure the composition of the soil sample, by measuring actual size and/or texture of the soil particles, thereby enabling the percentage composition of each of the soil particle types (e.g., sand, silt, and clay) to be calculated by the image processing unit 46. For example only, when only the sand, silt and clay particle categories are determined to be present in the soil sample 12, the sand category might constitute 50% of the total soil sample, the silt category might constitute 25% of the total soil sample, and the clay category might constitute 25% of the total soil sample. Given that the level of magnification is known and the image resolution is predetermined (e.g. around two micrometers, in at least the present embodiment of the device), the image processing unit 46 is able to separate the soil particles into their respective size categories: clay—below two micrometers; sand—above 50 micrometers; and silt—between clay and sand.

Although certain soil types and series may still require calibration of the apparatus to achieve a desired level of reliability, in other cases there may be no need for sensor calibration at all. The accuracy of the measured results provided by the present apparatus 10 are at least favorably comparable with those of conventional soil analysis currently conducted in analytical soil laboratories, which are more costly and/or more time consuming to conduct. Standard measurement errors may range between 30 and 60 g per kg of soil, which is comparable to the observed dispersion among results obtained from different commercial soil labs.

In addition to the image texture information of the soil particles as measured from the image of sample, color information measured from the image is also suitable to predict soil organic matter content, which is another useful soil property when it comes to optimized management of soil resources. Wth proper calibration, soil organic matter content in mineral soil can be predicted with a standard error of measurements around 5 to 7 g per kg of soil (i.e. 0.5-0.7% soil organic matter).

In an alternate embodiment, the apparatus 10 includes a container 50 defining an enclosure for receiving the soil sample 12. The container 50 is removably mounted in the head 16A of the housing 14 within the cavity 30. The container 50 has a transparent bottom surface abutting the window 32. In this particular embodiment, the soil sample 12 is not in direct contact with the window 32.

The cavity 30 and window 32, the lens assembly 44, and the image capturing device 36, are therefore disposed in a vertically sequential stacked alignment along the longitudinal axis 20 from the head 16A at the upper end 16 of the device to the base 18A at the lower end 18 thereof. Accordingly, the image capturing device 36 is located at the lowest elevation within the apparatus, the cavity 30 and transparent sample-receiving surface of the window 32 are at the highest elevation of the apparatus, and the lens assembly 44 is positioned there between. The light beams are provided in a direction from the base 18A toward the soil sample 12. However, due to the vertically highest position of the cavity 30 and the transparent sample-receiving surface of the window 32 therein, and the fact that this cavity and sample window 32 are open to atmosphere and not substantially blocked by another above them, any heat generated by the light source which might can evaporate water content in the soil sample 12 and any moisture already retained in or produced within the soil sample 12, is free to escape the soil sample. The vertically stacked alignment of the components 30, 44, 36 of the apparatus 10, and the fact that the cavity 30 receiving the soil sample is located at the highest elevation of the apparatus and is vertically open to atmosphere, thus allows the moisture to escape from the soil sample, such as through the opening 34. Consequently, no moisture build-up occurs within the soil sample before, during, or after testing.

Figure 3:
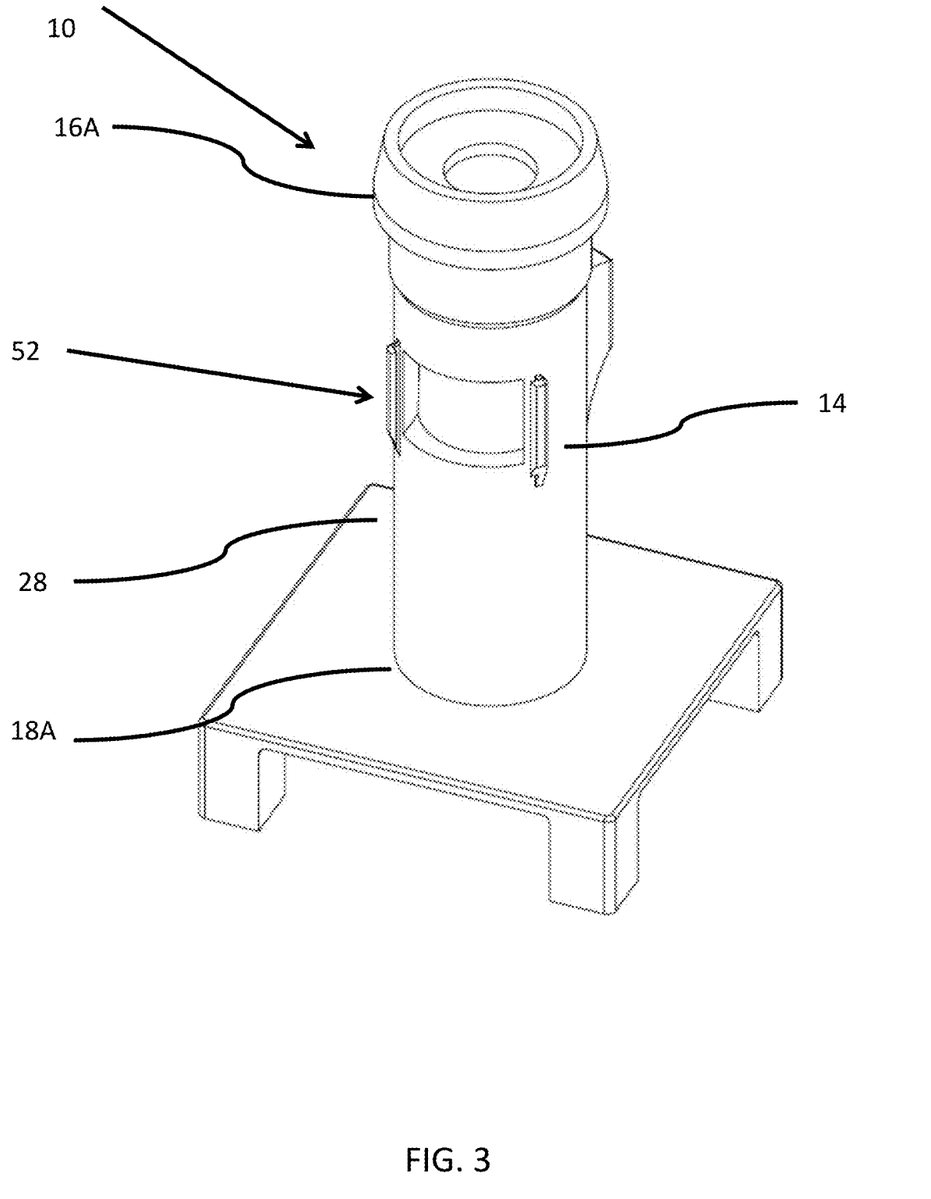
FIG. 3 is a schematic view of the apparatus of FIG. 1.

Referring to FIG. 3, an opening 52 may be provided in the side wall 28 of the housing 14. The opening 52 can be covered by a sliding cover, and the cover may be manipulated by a user to manually operate the lens assembly 44 (FIG. 2) over the range of magnifications. In another embodiment, the lens assembly 44 is digitally operated.

The above description is meant to be exemplary only, and one skilled in the art will recognize that changes may be made to the embodiments described without departing from the scope of the invention disclosed. Still other modifications which fall within the scope of the present invention will be apparent to those skilled in the art, in light of a review of this disclosure, and such modifications are intended to fall within the appended claims.

The invention claimed is:

1. An apparatus for analysing a sample of granular material, the apparatus comprising:
    an elongated housing extending between a top and an bottom spaced apart axially along a longitudinal axis, and a channel extending through the elongated housing to define an optical path;
    a cavity defined within the top of the housing to receive the sample, the cavity being at least partially open to a surrounding of the apparatus;
    a transparent sample-receiving surface disposed within the cavity at a first elevation from the bottom along the longitudinal axis, the transparent sample-receiving surface being in optical communication with the optical path;
    a lens assembly positioned within the optical path and extending thereacross at a second elevation from the bottom along the longitudinal axis, the lens assembly magnifying an image formed at least by light beams reflected by or transmitted through the sample, the second elevation being smaller than the first elevation such that the lens assembly is lower than the transparent sample-receiving surface;
    an image capturing device disposed across the optical path at a third elevation from the bottom along the longitudinal axis to capture an image, the third elevation being smaller than the second elevation such that the image capturing device is lower than both the lens assembly and the transparent sample-receiving surface; and
    a light source mounted within the housing to emit light toward the sample-receiving surface.

2. The apparatus as defined in claim 1, wherein the light source includes an array of light emitting diodes.

3. The apparatus as defined in claim 1, wherein the sample-receiving surface, the lens assembly and the image capturing device are provided coaxially in a vertically sequential stacked alignment along the longitudinal axis and within the optical path.

4. The apparatus as defined in claim 1, wherein the housing has an opening defined between an outermost surface of the housing and the cavity, the sample being receivable into the cavity through the opening.

5. The apparatus as defined in claim 1, comprising an image processing unit in communication with the image capturing device, the image processing unit is configured for receiving the image from the image capturing device and measuring a percentage of the granular material according to predefined size intervals based on texture information of the granular material captured by the image.

6. The apparatus as defined in claim 5, wherein the image processing unit is configured for identifying colors of the image and predicting organic matter content of the sample based on the identified colors.

7. The apparatus as defined in claim 5, wherein the image processing unit is configured for storing the percentage of the granular material according to the predefined size intervals in a cloud database.

8. The apparatus as defined in claim 1, wherein the image capturing device is configured for storing the image in a cloud database.

9. The apparatus as defined in claim 1, wherein the sample-receiving surface is made from a scratch resistant material.

10. The apparatus as defined in claim 1, comprising a container receivable in the cavity, the container receiving the sample and having a transparent surface abutting the sample-receiving surface.

11. The apparatus as defined in claim 1, wherein the lens assembly is equidistant from the sample-receiving surface and the image capturing device.

12. The apparatus as defined in claim 1, wherein the sample is a soil sample and the granular material contains soil particles.

13. The apparatus as defined in claim 5, wherein the sample is a soil sample and the granular material includes sand, silt and clay, and wherein the image processing unit identifies soil particles having a size of greater than 50 micrometers as sand, soil particles having a size of less than 2 micrometers as clay, and soil particles having a size between 2 and 50 micrometers as silt.

\* \* \* \* \*